United States Patent
Buzug et al.

(10) Patent No.: US 10,656,224 B2
(45) Date of Patent: May 19, 2020

(54) MAGNETIC FIELD-GENERATING DEVICE FOR MAGNETIC PARTICLE IMAGING

(71) Applicant: Universitat Zu Lubeck, Lubeck (DE)

(72) Inventors: Thorsten Buzug, Groß Sarau (DE); Matthias Weber, Lubeck (DE)

(73) Assignee: Universitat Zu Lubeck, Lubeck (DE)

( * ) Notice: Subject to any disclaimer, the term of this patent is extended or adjusted under 35 U.S.C. 154(b) by 147 days.

(21) Appl. No.: 15/761,772

(22) PCT Filed: Sep. 21, 2016

(86) PCT No.: PCT/EP2016/072342
§ 371 (c)(1),
(2) Date: Mar. 20, 2018

(87) PCT Pub. No.: WO2017/050789
PCT Pub. Date: Mar. 30, 2017

(65) Prior Publication Data
US 2019/0101604 A1    Apr. 4, 2019

(30) Foreign Application Priority Data
Sep. 21, 2015   (DE) .......................... 10 2015 218 122

(51) Int. Cl.
*G01R 33/383* (2006.01)
*H01F 7/02* (2006.01)
*A61B 5/05* (2006.01)

(52) U.S. Cl.
CPC .......... *G01R 33/383* (2013.01); *A61B 5/0515* (2013.01); *H01F 7/0278* (2013.01)

(58) Field of Classification Search
None
See application file for complete search history.

(56) References Cited

U.S. PATENT DOCUMENTS

| | | |
|---|---|---|
| 4,355,236 A | 10/1982 | Holsinger |
| 4,862,128 A | 8/1989 | Leupold |
| 2003/0099067 A1* | 5/2003 | Farahat ................ G11B 5/5526 360/264.3 |

(Continued)

FOREIGN PATENT DOCUMENTS

EP    1876462    1/2008

OTHER PUBLICATIONS

Hiltonj. "Halbach Cylinder." Wikimedia Commons. Accessed Jun. 6, 2018. https://commons.wikimedia.org/wiki/File:Halbach_cylinder.png#/mediaFile:Halbach_cylinder.png.

(Continued)

*Primary Examiner* — Paresh Patel
(74) *Attorney, Agent, or Firm* — Diederiks & Whitelaw, PLC.

(57) ABSTRACT

Disclosed is a device for simply creating a magnetic gradient field having a field-free line (FFL). The device comprises two ring-shaped Halbach arrays formed of permanent magnets, and preferably also a coil arrangement for electrically generating a homogeneous magnetic field for shifting the FFL in a predetermined plane. The FFL can be rotated together with the Halbach array in the plane, without the coil arrangement having to be rotated or moved. The invention is suitable for effective construction of a scanning device for magnetic particle imaging (MPI).

19 Claims, 4 Drawing Sheets

(56) References Cited

U.S. PATENT DOCUMENTS

2015/0177343 A1   6/2015   Wald et al.

OTHER PUBLICATIONS

Knopp et al. "Generation of a static magnetic field-free line using two Maxwell coil pairs." *Applied Physics Letters* 97, No. 9 (2010): 092505-1-092505-3.

Konkle et al. "Development of a field free line magnet for projection MPI." In *Medical Imaging 2011: Biomedical Applications in Molecular, Structural, and Functional Imaging*, vol. 7965, p. 79650X-1-79650X-7. International Society for Optics and Photonics, 2011.

\* cited by examiner

MAGNETIC FIELD-GENERATING DEVICE FOR MAGNETIC PARTICLE IMAGING

BACKGROUND OF THE INVENTION

The invention relates to a magnetic-field generating device that exhibits in particular permanent magnets in a Halbach arrangement. The magnetic field that has been generated exhibits a field-free line having a predetermined magnetic-field gradient in a predetermined plane that can serve as a scan plane for Magnetic Particle Imaging.

During Magnetic Particle Imaging (MPI), local concentrations of magnetizable nanoparticles are determined in an a priori unknown spatial distribution inside a patient. These nanoparticles are not radioactive and the MPI measurement method in addition does not require any ionizing radiation. For example super paramagnetic iron-oxide particles can be magnetized periodically by a drive field that can be changed periodically at a predetermined frequency, the magnetization of the particles being a non-linear function of the strength of the magnetic field. By detecting and analyzing the temporal behavior of the particle magnetization relative to the characteristic of the drive field, the particle concentration can be inferred.

For narrowing down the MPI measurement to small volumes of the patient, the drive field is superposed by a normally temporally constant selection field. The selection field has a zero at at least one predetermined point of the analysis region. Starting from this, a so-called field-free point, FFP for short, a selection field quickly increases in all directions so that the magnetizable nanoparticles reach magnetic saturation even at a short distance from the FFP. Nanoparticles at a great distance from the FFP then hardly react to the drive field and do not contribute significantly to the detected signal. The MPI measurement signal rather originates from the local surroundings of the FFP and informs on the local particle concentration that is present there.

As an alternative, it is also possible to generate instead of a single FFP a field-free line, FFL for short, for example using a suitable configuration of magnetic-field generating coils. Using an FFL instead of a single FFP has the potential to reduce the data acquisition duration by one order of magnitude. However, all magnetic particles of an object placed inside the coil arrangement along the FFL respond simultaneously to a change in the drive field so that evaluating the MPI measurement signals in terms of local concentrations that can then be assigned to individual voxels of the object, requires a numerically more complex effort than for only one FFP.

It is prior art to shift the position of an FFP or an FFL inside a region from which the MPI measurement data are to be obtained—the so-called field of view, FOV—by superposing a time-varying homogenous magnetic field on the static selection field. Specifically for the MPI having an FFL, this homogenous magnetic field is to be applied at right angles to the course of the FFL and on account of its field direction also determines along which plane the FFL can be shifted. As a result of, the scan plane of the MPI through which in the ideal case a patient is to be moved through at right angles, is established.

For the numerically more complex treatment, mentioned above, of the MPI measurement data when using an FFL it is important that the FFL can be rotated inside the scan plane about its center point, i.e., that the MPI signal detection can take place in a manner comparable to an x-ray CT measurement with a plurality of orientations of the FFL relative to the resting patient. The homogenous magnetic field that always serves the scanning lateral movement of the FFL in the scan plane, therefore up to now has to be generated by a coil pair that accompanies the rotary movement of the FFL also in terms of instruments, i.e. the coil arrangement has to be designed so as to be rotatable at least within limits. This represents a disadvantage both in terms of material wear and also handling of the high-voltage carrying leads to the coil pair.

The person skilled in the art knows so-called Halbach arrangements of permanent magnets. Such arrangements can in particular be designed as geometrical objects in which a plurality of permanent magnets, for example in rod shape, are present embedded in a predetermined arrangement. Such objects usually consist of a non-magnetic material matrix, are for example shaped bodies from a cured polymer such as e.g. polymethyl methacrylate (PMMA) and comprise strong permanent magnets based on rare-earth elements. The objects themselves then exhibit permanent magnetic fields whose flux densities in part areas of their surface can be larger than the largest flux density of any of the embedded permanent magnets. The objects comprising a Halbach arrangement at the same time also exhibit part areas of their surface that are virtually free from any magnetic field.

Among the most prominent examples for geometrical objects comprising Halbach arrangements are the Halbach cylinders. Such cylinders have an inside and an outside diameter and in this respect consist of a material that forms a thick cylinder jacket, i.e. a tube. A Halbach cylinder is characterized in that in the course of the jacket the magnetization direction of the jacket exhibits a constant rotation in the plane at right angles to the cylinder axis. Since the jacket is closed, the magnetization direction returns to its starting value in the case of one rotation of the entire cylinder jacket. For clarification, reference is made to FIG. 1. (Source: "Halbach cylinder" by Own work by en:User:Hiltonj—originally uploaded to the English language Wikipedia. Licensed under CC BY-SA 3.0 via Wikimedia Commons—https://commons.wikimedia.org/wiki/File:Halbach_cylinder.png #/media/File:Halbach_cylinder.pnq).

When expressed in plane polar coordinates R, φ, the—two-dimensional—magnetization vector of a Halbach cylinder jacket is described by $\vec{M}=M_0 (\cos k\varphi, \sin k\varphi)$, k having to be a natural number and often being described as a Halbach order.

FIG. 1 shows diagrams of the Halbach cylinders of the first four orders with the predetermined magnetization directions of the jacket material and the magnetic-field directions, resulting therefrom, in the—material-free—inside spaces of the cylinders. Obviously, a Halbach cylinder of the Halbach order k=2 is of particular practical interest since it is capable of providing a relatively strong homogenous magnetic field at right angles to the cylinder axis in its interior.

In principle, the magnetic field of an ideal Halbach cylinder can be precisely calculated analytically. However, since in practice Halbach cylinders are produced from a finite number of permanent-magnetic segments anyway and consequently the rotation of the magnetization direction in the cylinder jacket takes place in discrete steps, the analytical calculation can hardly be handled for real devices. Rather the numeric simulation of the magnetic field inside the cylinder is resorted to. Here it is quickly recognized that the homogeneity of the magnetic field for a cylinder of the Halbach order k=2 for a real arrangement is of course only an approximation and in this case is not even a good one for the vicinity of the cylinder top surfaces. As a matter of principle, the cylinder height may not be selected to be too small if the postulated geometry of the magnetic field is to be achieved at least in part areas of the cylinder inside.

In comparison to the inside diameter of the cylinder, the cylinder height is usually large, often even larger than the outside diameter. Directing and focusing charged particle beams is among the known applications of Halbach cylinders of the Halbach order k=3.

It is in particular Knopp et al. "Generation of a static magnetic field-free line using two Maxwell coil pairs", APPLIED PHYSICS LETTERS 97, 092505, 2010, that mentions the current-less generation of an FFL in the quadrupole field of a Halbach cylinder of the Halbach order k=3 as a possibility for the MPI. However, this FFL at first is on the axis of symmetry of the Halbach cylinder along which e.g. a patient would have to be pushed in. In this respect, the FFL has at first to be rotated by 90° into a suitable scan plane, and then also two coil pairs for shifting the FFL in the scan plane have to be arranged. The work by Knopp et al. circumvents this by replacing the Halbach cylinder by two pairs of Maxwell coils, it now being possible to move the patient along an axis through one of the coil pairs.

Halbach cylinders having the Halbach order k=2 are already applied as current-free generators of homogenous magnetic fields even in the case of magnetic resonance tomography—MRT—, as can be gathered from the printed matter US 2015/177343 A1. It shall only be emphasized here that the field of view is in the cylinder inside in the work mentioned.

There also exist further applications of Halbach cylinders in magnetic gears. Here a plurality of Halbach cylinders—usually of differing Halbach orders—is arranged placed inside each other concentrically. A rotational movement of one of the cylinders is transmitted contact-free to the other as a result of the magnetic interaction. In magnetic gears, the cylinder height is in part rather small, often markedly smaller than the outside diameter.

The printed matter EP 1876462 A1 uses a plurality of stacks of Halbach rings that are placed inside each other concentrically and can be rotated relative to each other so that the magnetic field can be fine-tuned as precisely as possible inside the concentric stacks.

SUMMARY OF THE INVENTION

For Halbach cylinders whose height is designed to be smaller than the outside diameter, the present description also uses the term "Halbach ring" below. The cylinder height for Halbach rings is also termed the "ring width" below.

In the following text, a Halbach ring of the Halbach order k=2 is in addition assigned a magnetization direction that matches the direction of the magnetic field inside the Halbach ring. The magnetization direction of such a Halbach ring is in particular at right angles on the axis of symmetry of the ring. Here the axis of symmetry of the ring is also termed as the "ring axis". The center point of a Halbach ring is the geometrical center point. It is situated inside a ring on the ring axis and coincides with center of gravity if the ring is e.g. formed from a material having a homogenous mass density.

It is now the object of the invention to propose a magnetic-field generating device for the MPI that provides a selection field having an FFL in a simple and energy-saving manner, it being additionally possible to shift and rotate the FFL in a scan plane without any angular limitation.

The object is achieved by a magnetic-field generating device exhibiting two structurally identical Halbach rings, formed from permanent magnets, of the Halbach order k=2 having in each case a predetermined inside diameter and outside diameter and predetermined ring width and magnetization direction, characterized in that the Halbach rings having a center-point distance greater than the ring width and smaller than the outside diameter are arranged symmetrically relative to a plane of symmetry, the projections of the magnetization directions onto the plane of symmetry pointing in opposite directions.

The center-point distance is the geometrical distance of the center points of both rings.

The most simple and at the same time preferred manner of symmetrically arranging the Halbach rings consists in arranging the rings coaxially, i.e. that their ring axes are located on the same straight line.

If the rings were placed directly one on top of the other, so that the rings together would form a new ring having twice the ring width of a single ring, the center-point distance would just precisely amount to this ring width. This is not sufficient. The distance has to be greater so that the two Halbach rings form an arrangement having an air gap. The plane of symmetry of the arrangement lies in the center of this air gap.

Insofar as the Halbach rings exhibit inside diameters greater than two ring widths—in other words: the ring widths are designed to be smaller than the inside radii—, then it is a preferred embodiment of the invention if the Halbach rings are arranged at a center-point distance at least greater than half the inside diameter.

The coaxially arranged Halbach rings are rotated relative to each other by 180° about their common axis, so that their magnetization directions point in opposite directions.

If the arrangement described so far is made the subject of a numerical modeling of the generated magnetic field and if in the process in particular the plane of symmetry is analyzed, then the following can be found:
1. There is a field-free line in the plane of symmetry. This FFL is in a good approximation a straight line.
2. Outside the FFL in the plane of symmetry, the absolute value of the magnetic field increases with a field gradient that permits applications in the MPI if the Halbach rings are equipped with correspondingly strong magnets.
3. Across an extended area of the plane of symmetry, the magnetic field that has been generated exhibits only field components along the common axis of the Halbach rings, that is to say at right angles to the plane of symmetry.
4. If an additional homogenous magnetic field is applied along the Halbach ring axes that varies over time, the FFL can be shifted in the plane of symmetry as a result.

In addition, it is immediately obvious to the person skilled in the art that the direction of the FFL can be rotated jointly with the two Halbach rings. It is therefore a particularly preferable embodiment of the device for the Halbach rings to be mounted so as to be rotatable about their ring axes. Here they should always rotate simultaneously and in the same manner so as to maintain the properties of the magnetic field in the plane of symmetry—that can serve as the scan plane for the MPI thereafter. The device therefore preferably also comprises a mechanical gear for transmitting the rotation of a Halbach ring to the other while maintaining the opposite magnetization directions of the Halbach rings.

However, an electric coil arrangement that provides a homogenous magnetic field for shifting the FFL at no time has to be moved or rotated for in this case the magnetic field is to be applied parallel to the axis of rotation. Thus the device is preferably expanded by a coil arrangement, particularly preferably a Helmholtz coil pair, designed for generating a homogenous magnetic field having a field direction at right angles to the plane of symmetry of the Halbach ring arrangement at least in a part area of the plane of symmetry.

It can further represent an advantage if the device is not constructed having precisely coaxial Halbach rings but also considers tilting the Halbach rings. Here tilting has to take place such that the arrangement of the rings always remains symmetrical relative to a plane of symmetry. For example the two Halbach rings can be inclined toward each other by the same tilting angle. This preferably produces a symmetric arrangement of the Halbach rings that exhibits a predetermined tilting angle of the ring axes greater than zero toward the normal of the plane of symmetry. The absolute value of the tilting angle should preferably be chosen to be in the range 5° to 15°.

In the tilted arrangement, too, the Halbach rings can be rotated about their ring axes, again both having to be rotated simultaneously and in the same manner. Even though the magnetization directions of the Halbach rings due to the tilting are no longer positioned such that they can be aligned precisely in opposite directions relative to each other, however this is not essential. In fact it is important that the projections of the magnetization directions onto the plane of symmetry point in opposite directions, so that the field conditions suitable for MPI appear precisely there.

The person skilled in the art can readily model the magnetic field of such an arrangement of the Halbach rings. This can be discovered:
1. There is still an FFL in the plane of symmetry, however it can only approximately be classified as a straight line. In comparison to the FFL in the case of coaxial rings it is here present shifted in the direction toward the greatest approximation of the tilted Halbach rings.
2. The field gradient in the vicinity of the FFL is no longer as uniform as in the case of the coaxial rings, but still sufficient for MPI in terms of absolute value.
3. In a good approximation the magnetic field still only exhibits field components at right angles to the plane of symmetry over a large area of the plane of symmetry.
4. The homogenous magnetic field of a coil arrangement—the coils are not to be tilted with the Halbach rings—is still suited to shift the FFL in the scan plane.

The advantage of the tilted arrangement that can be recognized is the current-less repositioning of the FFL in the scan plane, therefore in the adjustable position of the FFL without the field of the coils.

When a patient—or a body part of a patient—is moved through the scan plane and thus also through the interior spaces of the Halbach rings, the FFL eventually has to be shifted into a region of interest (ROI) in the patient in which the MPI scan is to take place if it is not desired to scan the entire patient. This can be achieved by a suitably selected basic energization of the coils that for example deflects the FFL from its central position in the case of the coaxial Halbach rings. But the energization of the coils is limited, partly for technical reasons and partly for medical ones. This is because for the MPI scan the position of the FFL in the ROI is to be typically varied at a kilohertz frequency and the higher the strength of the magnetic field generated by the coils has to be, the more likely it is that undesirable physiological effects occur, e.g. a peripheral nerve stimulation (PNS).

Tilting the Halbach rings creates a new degree of freedom for positioning the FFL, to be precise the tilting angle. Here the magnetic field is at first temporally constant and the FFL is so to say shifted from a new "rest position" in the case of the MPI scan, and this at least should also reduce the energy consumption of the coils.

During the joint rotation of the tilted Halbach rings, however, the FFL is not rotated on its own in the scan plane but at the same time also translated and possibly also slightly deformed. For MPI evaluation this means that quite simply it becomes more complicated and presumably more complex numerically. No such evaluation exists as of today and is also not a subject of this invention.

However the magnetic fields of the inventive device can be computed by the person skilled in the art using appropriate—commercially available—modeling software for each specific embodiment of the Halbach rings. Without any mental effort, to be precise according to the principle of trial and error, he can vary the distances of the Halbach rings so as to generate a gradient field in the plane of symmetry that is for example as uniform and as linear as possible for his purposes using an FFL that is as straight as possible. But he can also compute the course of the FFL for each rotated and/or tilted state of the Halbach rings with a high degree of precision and record it for later processing. In this respect, the feasibility in principle of an MPI measurement using the invention is therefore not in question even in the case of tilted rings.

The MPI evaluation can be readily adapted from the known prior art for the device having coaxially arranged Halbach rings. For this reason, the invention is suited for generating a selection field for Magnetic Particle Imaging.

BRIEF DESCRIPTION OF THE DRAWINGS

The following explanations and figures serve to clarify the invention using an exemplary embodiment. In the figures.

DETAILED DESCRIPTION OF THE INVENTION

Figure 1:
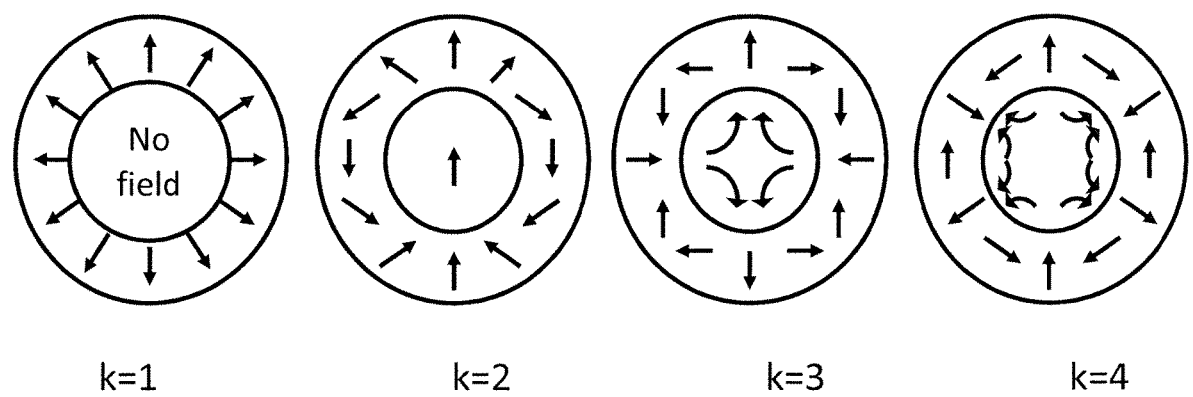
FIG. 1 shows diagrams of Halbach cylinders of the first four orders according to the prior art.
Figure 2:
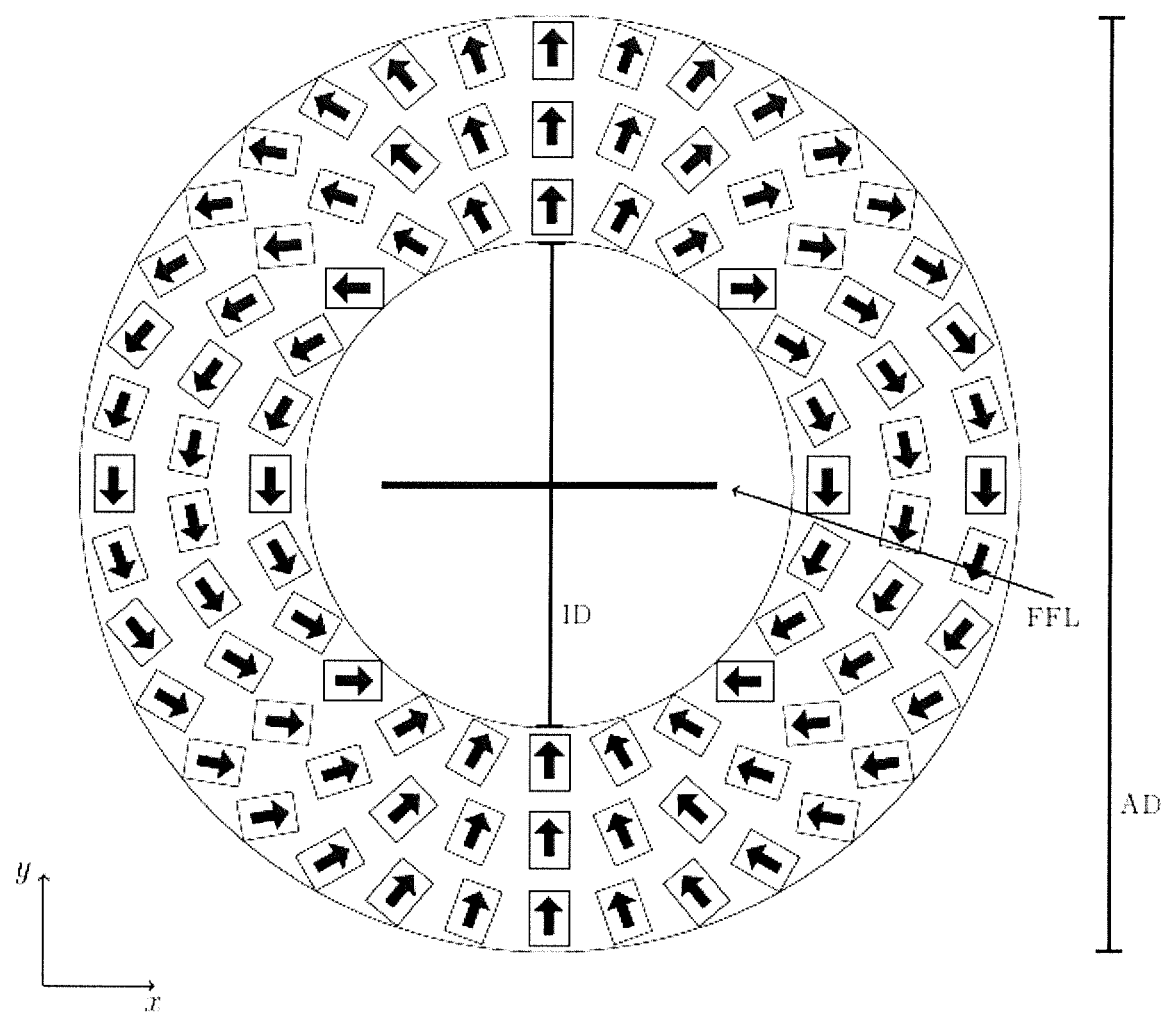
FIG. 2 shows the top-view sketch (xy plane) of an annular arrangement of discrete cuboid permanent magnets arranged in three concentric circles.
Figure 3:
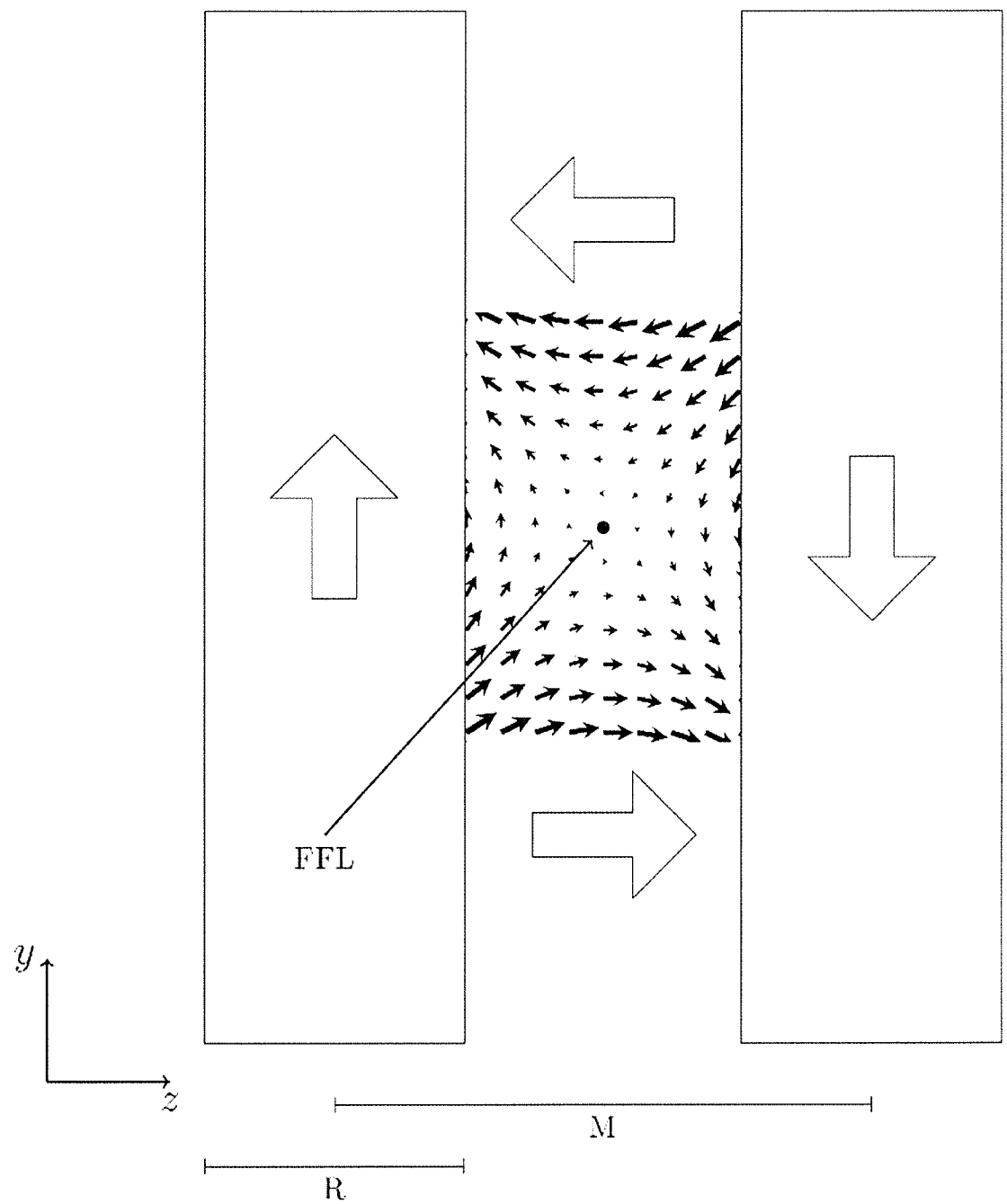
FIG. 3 the side-view sketch (yz plane) of the arrangement of two Halbach rings according to the teachings of the invention with an illustration of the magnetic field in the air gap.

The device shown in FIGS. 2 and 3 is dimensioned such that it permits MPI measurements on small animals, e.g. on mice.

FIG. 2 shows the construction of one of the Halbach rings that is composed of cuboid permanent magnets—consisting of neodymium iron boron having a remanence of 1.42 Tesla and the magnetization property N52—in a non-magnetic plastic matrix. Here the plastic matrix is produced by means of a 3D printer. Almost all printable, curable polymers are suitable as a plastic matrix. The cuboids have a size of 42 mm×10 mm×7.2 mm and are magnetized along the 10 mm side. The Halbach ring comprises 90 individual magnets, the magnets being distributed over three rings having (from inside to outside) in each case 24, 30 and 36 magnets. The magnets are arranged in circles having the radii 49.6 mm, 63.6 mm and 77.6 mm. Here the arrows represent the local magnetization direction. The Halbach ring exhibits an inside diameter ID of 87 mm, an outside diameter AD of 167.6 mm and a ring width R of 42 mm. The magnetization direction of the Halbach ring points exactly into the y direction, while the ring axis extends into the drawing plane, in the z direction.

FIG. 2 also shows the position of the field-free line FFL in the inventive arrangement. Important: The FFL shown is no product of the one Halbach ring illustrated in FIG. 2. It is not produced until in the arrangement of FIG. 3.

FIG. 3 shows two Halbach rings according to FIG. 2 in the side view (yz plane), the magnetization directions of the rings or the projections of the magnetization directions onto the plane of symmetry of the arrangement pointing in opposite directions. The field components resulting from the arrangement cancel each other precisely at the center so that the field-free line FFL is produced there. It must be emphasized here that the center-point distance M of the Halbach rings of 87 mm is not only larger than the ring width R or than half the inside diameter ID, but in the example precisely corresponds to the inside diameter ID of the rings.

Here it is to be understood that the center-point distance M is an optimization parameter that the person skilled in the art has to determine for himself once using a numerical modeling of different distances of the rings in view of his specific Halbach rings. For him this will not be difficult as a one-time pre-analysis using commercially available software. Here he can evaluate the resulting field in accordance with his own optimality criteria.

In the present example, the straightness of the FFL and the uniformity of the magnetic-field gradient in the vicinity of the FFL were optimized. The fact that modeling for the purpose of optimizing here has a result that the center-point distance M is to precisely correspond to the inside diameter ID cannot be readily regarded as a general rule. However, as a rule of thumb it can very well be recommended to start the search for the center-point distance M of the Halbach rings for a suitable MPI selection field in the area of the inside diameter ID of the rings even if the ring width R is markedly smaller than the inside diameter ID or, as in the example, even smaller than half the inside diameter ID.

As FIG. 3 further shows, precisely in the plane of symmetry only field components in the z-direction, i.e. along the ring axes, are present. The large arrows indicate the local main-magnetic-field direction, the arrows drawn in the rings at the same time also corresponding to the magnetization directions of the Halbach rings. The small arrows in the air gap between the rings describe the local magnetic-field direction and, by their length, the strength of the magnetic field that can be computed by means of numerical modeling of the magnetic field of the inventive arrangement.

Figure 4:
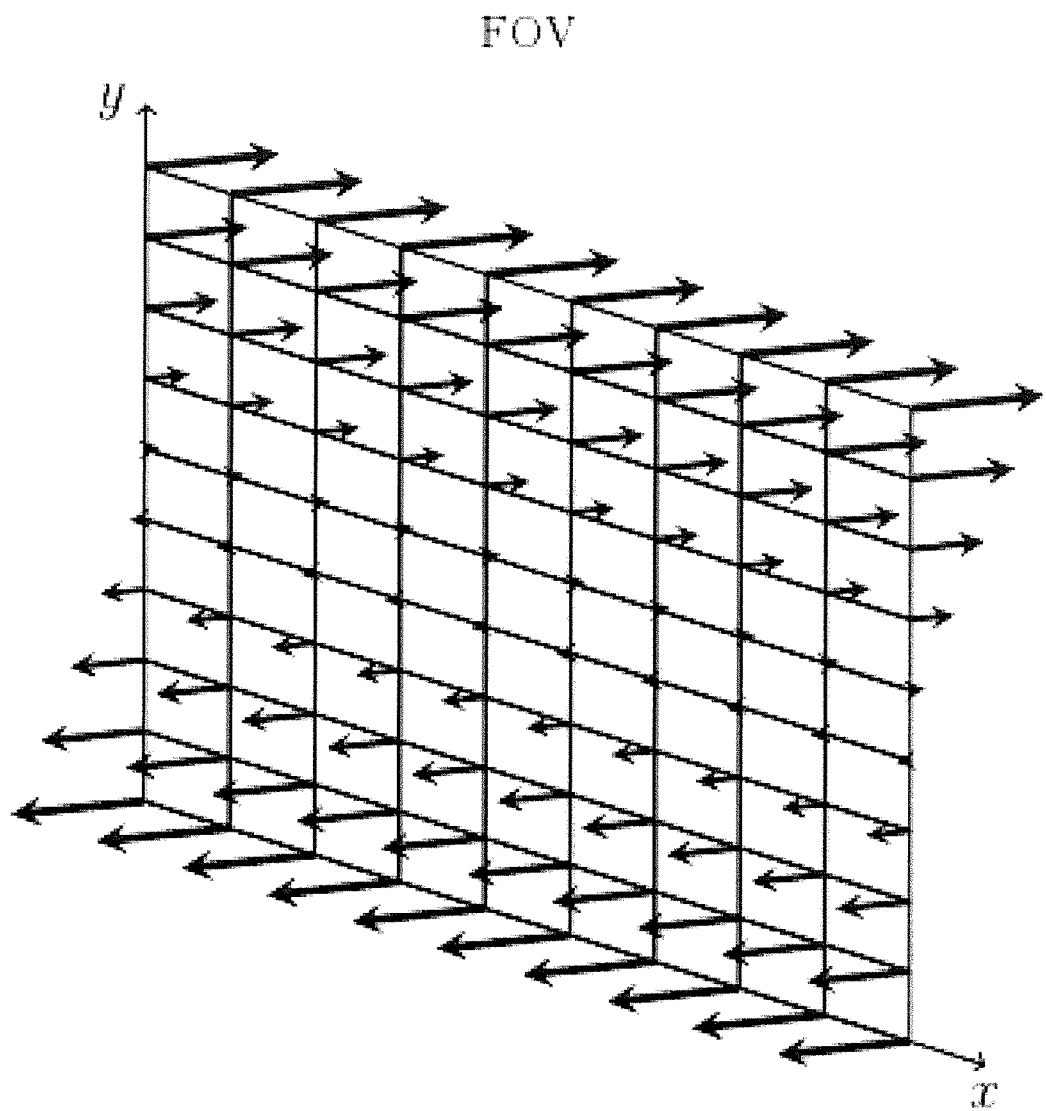
FIG. 4 shows a sketch of the magnetic-field components in the plane of symmetry (xy plane) of the arrangement of the Halbach rings.

For the purposes of MPI, the magnetic field in the plane of symmetry of the arrangement, that is to serve as the scan plane for the FFL, is of particular importance. FIG. 4 shows the result of numerical modeling precisely for this plane. Only z components of the magnetic field occur over an extended area of approximately 50 mm×50 mm. This area defines the FOV of the MPI in which the FFL can now be shifted through a homogenous magnetic field aligned along the ring axes (z axis). This also holds for any simultaneous rotations of the two Halbach rings carried out in the same way.

The invention claimed is:

1. A magnetic-field generating device exhibiting two structurally identical Halbach rings, formed from permanent magnets, of the Halbach order k=2 having in each case a predetermined inside diameter ID and outside diameter AD and predetermined ring width R and magnetization direction, characterized in that: the Halbach rings having a center-point distance M greater than the ring width R and smaller than the outside diameter AD are arranged symmetrically relative to a plane of symmetry, with projections of the magnetization directions onto the plane of symmetry pointing in opposite directions; and a coil arrangement, preferably a Helmholtz coil pair, formed for generating a homogenous magnetic field having the field direction at right angles to the plane of symmetry of the Halbach rings at least in a part area of the plane of symmetry.

2. The magnetic-field generating device according to claim 1, characterized in that the Halbach rings exhibit inside diameters ID greater than two ring widths R and are arranged at a center-point distance M greater than half the inside diameter ID.

3. The magnetic-field generating device according to claim 1, characterized in that the Halbach rings are arranged coaxially.

4. The magnetic-field generating device according to claim 1, characterized in that the symmetric arrangement of the Halbach rings exhibits a predetermined tilting angle of the ring axes greater than zero relative to the normal of the plane of symmetry.

5. The magnetic-field generating device according to claim 4, characterized in that the tilting angle is predetermined from the interval 5° to 15°.

6. The magnetic-field generating device according to claim 1, characterized by a unit designed for temporally periodically energizing the coil arrangement.

7. The magnetic-field generating device according to claim 1, characterized in that the Halbach rings are mounted so as to be rotatable about their ring axes.

8. The magnetic-field generating device according to claim 7, characterized by a mechanical gear for transmitting the rotation of one Halbach ring to the other while maintaining the opposite magnetization directions of the Halbach rings.

9. Use of a device according to claim 1 for generating a selection field for Magnetic Particle Imaging.

10. The magnetic-field generating device according to claim 2, characterized in that the Halbach rings are arranged coaxially.

11. The magnetic-field generating device according to claim 2, characterized in that the symmetric arrangement of the Halbach rings exhibits a predetermined tilting angle of the ring axes greater than zero relative to the normal of the plane of symmetry.

12. The magnetic-field generating device according to claim 2, characterized by a coil arrangement, preferably a Helmholtz coil pair, formed for generating a homogenous magnetic field having the field direction at right angles to the plane of symmetry of the Halbach rings at least in a part area of the plane of symmetry.

13. The magnetic-field generating device according to claim 3, characterized by a coil arrangement, preferably a Helmholtz coil pair, formed for generating a homogenous magnetic field having the field direction at right angles to the plane of symmetry of the Halbach rings at least in a part area of the plane of symmetry.

14. The magnetic-field generating device according to claim 4, characterized by a coil arrangement, preferably a Helmholtz coil pair, formed for generating a homogenous magnetic field having the field direction at right angles to the plane of symmetry of the Halbach rings at least in a part area of the plane of symmetry.

15. The magnetic-field generating device according to claim 5, characterized by a coil arrangement, preferably a Helmholtz coil pair, formed for generating a homogenous magnetic field having the field direction at right angles to the plane of symmetry of the Halbach rings at least in a part area of the plane of symmetry.

16. The magnetic-field generating device according to claim 2, characterized in that the Halbach rings are mounted so as to be rotatable about their ring axes.

17. The magnetic-field generating device according to claim 3, characterized in that the Halbach rings are mounted so as to be rotatable about their ring axes.

18. The magnetic-field generating device according to claim 4, characterized in that the Halbach rings are mounted so as to be rotatable about their ring axes.

19. The magnetic-field generating device according to claim 5, characterized in that the Halbach rings are mounted so as to be rotatable about their ring axes.

\* \* \* \* \*